(12) United States Patent
Mao et al.

(10) Patent No.: US 10,964,410 B2
(45) Date of Patent: Mar. 30, 2021

(54) SYSTEM AND METHOD FOR DETECTING GENE FUSION

(71) Applicant: KONINKLIJKE PHILIPS N.V., Eindhoven (NL)

(72) Inventors: Yong Mao, Hawthorne, NY (US); Nevenka Dimitrova, Pelham Manor, NY (US); Kostyantyn Volyanskyy, Larchmont, NY (US)

(73) Assignee: Koninklijke Philips N.V., Eindhoven (NL)

(*) Notice: Subject to any disclaimer, the term of this patent is extended or adjusted under 35 U.S.C. 154(b) by 353 days.

(21) Appl. No.: 15/985,932

(22) Filed: May 22, 2018

(65) Prior Publication Data

US 2018/0341746 A1 Nov. 29, 2018

Related U.S. Application Data

(60) Provisional application No. 62/510,862, filed on May 25, 2017.

(51) Int. Cl.
*G16B 30/00* (2019.01)
*G16B 40/00* (2019.01)
(Continued)

(52) U.S. Cl.
CPC .............. *G16B 30/00* (2019.02); *G16B 40/00* (2019.02); *G16B 99/00* (2019.02); *G16H 50/20* (2018.01)

(58) Field of Classification Search
CPC ........ G16B 30/00; G16B 99/00; G16B 40/00; G16H 50/20
(Continued)

(56) References Cited

U.S. PATENT DOCUMENTS

2006/0134667 A1* 6/2006 Narahara ............. C12Q 1/6827
435/6.14
2009/0239221 A1* 9/2009 Chinnaiyan .......... C12Q 1/6886
435/6.16
(Continued)

FOREIGN PATENT DOCUMENTS

WO 2014172046 A2 10/2014
WO WO-2015149034 A2 * 10/2015 ........... C12Q 1/6886

OTHER PUBLICATIONS

Rowley JD. "A new consistent chromosomal abnormality in chronic myelogenous leukaemia identified by quinacrine fluorescence and giemsa staining". Nature. 1973, 243:290-293.
(Continued)

*Primary Examiner* — Michael Tomaszewski

(57) ABSTRACT

The present disclosure pertains to a system, a method of using such a system, and a non-transitory computer-readable medium containing instructions to such a system for generating annotated gene fusion data from processing both a patient's DNA and RNA sequence information thereby filtering out weak candidate gene fusions. Thus the annotated gene fusion data contains clinically relevant information and accurate gene fusion detections (low false-positives) for use in clinical and/or R&D settings. The system, method and computer-readable medium allows a user to generate gene fusion data by detecting breakpoints from a patient's DNA-SEQ and RNA-SEQ, creating candidate breakpoint data by combining matching breakpoints from the DNA-SEQ and RNA-SEQ breakpoint data, determining confidence levels of the candidate breakpoint, identifying corresponding gene fusions, and annotating clinically relevant information about the gene fusions.

24 Claims, 6 Drawing Sheets

(51) Int. Cl.
*G16B 99/00* (2019.01)
*G16H 50/20* (2018.01)

(58) Field of Classification Search
USPC .......................................................... 705/2–3
See application file for complete search history.

(56) References Cited

U.S. PATENT DOCUMENTS

| | | | | |
|---|---|---|---|---|
| 2014/0315199 | A1* | 10/2014 | Rhodes | C12Q 1/6886 435/6.11 |
| 2015/0315657 | A1* | 11/2015 | Rhodes | C12Q 1/6886 424/133.1 |
| 2017/0240972 | A1* | 8/2017 | Mokhtari | G16B 40/00 |

OTHER PUBLICATIONS

Demichelis F, Fall K, Perner S et al. TMPRSS2-ERG gene fusion associated with lethal prostate cancer in a watchful waiting cohort. Oncogene. 2007, 26:4596-4599.

McPherson, A., et al., deFuse: an algorithm for gene fusion discovery in tumor RNA-Seq data. PLoS Computational Biology, 2011. 7(5): p. e1001138.

Kim, D. and S.L. Salzberg, TopHat-Fusion: an algorithm for discovery of novel fusion transcripts. Genome Biology, 2011. 12(8): p. R72.

* cited by examiner

SYSTEM AND METHOD FOR DETECTING GENE FUSION

CROSS-REFERENCE TO RELATED APPLICATION

The present application claims the benefit of U.S. Provisional Application No. 62/510,862, filed May 25, 2017. These applications are hereby incorporated by reference herein.

FIELD

Various embodiments described herein are directed generally to biomedical informatics technology. More particularly, various methods, systems, and apparatus disclosed herein relate to detection of gene fusions associated with cancer using bioinformatics technology.

BACKGROUND

Cancer is a genetic disease caused by changes in genetic material. Gene fusion is one type of changes in genetic material involving structural rearrangements of chromosomes that cause exchange of DNA sequences between genes. It is well known that some gene fusions are associated with specific types of cancers (e.g., BCR-ABLE gene fusion is associated with myelogenous leukemia, and TMPRSS2-ERG gene fusion is associated with prostate cancer). Furthermore, certain cancer therapies have been developed that specifically target specific types of cancer caused by specific gene fusions. Thus, detection of gene fusions in patients is useful in diagnosing cancer and determining appropriate cancer treatment options.

In cancer diagnostics, gene fusion detection techniques such as fluorescence in situ hybridization and reverse-transcription polymerase chain reaction are available. However, these methods require prior knowledge of targeted gene fusions. Next generation sequencing (NGS) technology has the potential to be a powerful tool for detecting gene fusions in clinical settings. However, high false positive rates and low detection specificity in gene fusion data generated by NGS technology has been a problem for using NGS technology in clinical settings. Moreover, lack of clinically-relevant information being provided by NGS further hindered the application of NGS-generated gene fusion data in clinical settings.

SUMMARY

In various aspects, the invention provides a data processing system for providing clinically relevant gene fusion breakpoints and associated information, the system comprising: at least one memory operable to store a data repository; a sequencing platform communicatively coupled to the at least one memory; and a processor communicatively coupled to the at least one memory, the processor being operable to: (a) detect, using a DNA-SEQ breakpoint detection module, a first candidate breakpoint based on a DNA-SEQ data set by comparing the DNA-SEQ data set to a DNA reference sequence data set; (b) detect, using a RNA-SEQ breakpoint detection module, a second candidate breakpoint based on a RNA-SEQ data set by comparing the RNA-SEQ data set to both a DNA reference sequence data set and a RNA reference data set; (c) correlate, using a breakpoint data processing module, the first and second candidate breakpoints to generate a combined breakpoint list, characterized by a higher threshold specificity; (d) annotate, using a gene fusion data annotation module, the combined breakpoint list with biologically and clinically relevant information to generate an annotated gene fusion data set, wherein the combined breakpoint list of step (c) has a lower false-positive breakpoint detection rate compared to a false-positive breakpoint detection rate in the absence of the correlation in step (c) and wherein the annotated gene fusion data set is suitable for being used for having a clinical decision made.

In various aspects, the invention provides a computer-implemented method for providing clinically relevant gene fusion breakpoints and associated information, the method being based on disparate sequencing data sets and comprising: (a) detecting a first candidate breakpoint based on a DNA-SEQ data set by comparing the DNA-SEQ data set to a DNA reference sequence data set; (b) detecting a second candidate breakpoint based on a RNA-SEQ data set by comparing the RNA-SEQ data set to both a DNA reference sequence data set and a RNA reference data set; (c) correlating the first and second candidate breakpoints to generate a combined breakpoint list, characterized by a higher threshold specificity; (d) annotating the combined breakpoint list with biologically and clinically relevant information to generate an annotated gene fusion data set, wherein the combined breakpoint list of step (c) has a lower false-positive breakpoint detection rate compared to a false-positive breakpoint detection rate in the absence of the correlation in step (c), and wherein the annotated gene fusion data set is suitable for being used for having a clinical decision made.

In various aspects, the invention provides a non-transitory computer-readable medium comprising instructions which, when implemented by one or more computers, cause the one or more computers to perform steps including: (a) detecting a first candidate breakpoint based on a DNA-SEQ data set by comparing the DNA-SEQ data set to a DNA reference sequence data set; (b) detecting a second candidate breakpoint based on a RNA-SEQ data set by comparing the RNA-SEQ data set to both a DNA reference sequence data set and a RNA reference data set; (c) correlating the first and second candidate breakpoints to generate a combined breakpoint list, characterized by a higher threshold specificity; (d) annotating the combined breakpoint list with biologically and clinically relevant information to generate an annotated gene fusion data set, wherein the combined breakpoint list of step (c) has a lower false-positive breakpoint detection rate compared to a false-positive breakpoint detection rate in the absence of the correlation in step (c) and wherein the annotated gene fusion data set is suitable for being used for having a clinical decision made.

In various embodiments, the DNA-SEQ data set and the RNA-SEQ data set of step (a) are each obtained from a different sequencing platform.

In various embodiments, the step of comparing the DNA-SEQ data set to DNA reference sequence data set in step (a) comprises: optimizing structure of the DNA-SEQ data set by sorting, removing duplicates from, and indexing the DNA-SEQ data set; aligning the DNA-SEQ data set with the DNA reference sequence data set; determining a location of the candidate breakpoint relative to the DNA reference sequence data set; and collecting statistical evidence associated with the candidate breakpoint.

In various embodiments, the step of comparing the RNA-SEQ data set to both DNA reference sequence data set and RNA reference sequence data set in step (b) comprises: aligning the RNA-SEQ data set with the DNA reference sequence data set; optimizing structure of the RNA-SEQ data set by sorting and removing duplicates from the RNA-SEQ data set; aligning the RNA-SEQ data set with the RNA reference sequence data set; optimizing structure of the RNA-SEQ data set by sorting and removing duplicates from the RNA-SEQ data set; determining a location of the candidate breakpoint relative to the RNA reference sequence data set; and collecting statistical evidence associated with the candidate breakpoint.

In various embodiments, the step of correlating the first and second candidate breakpoints in step (c) comprises performing a cascading filtering, the cascading filtering comprising: removing the candidate breakpoint having low coverage and high breakpoints reported around the candidate breakpoint; removing the candidate breakpoint having large portion of supporting reads with low mapping quality; removing the candidate breakpoint having bias-distributed supporting read along two genomic strands; removing the candidate breakpoint with both ends located on homologous genes; and removing the candidate breakpoint with both ends located on adjacent genes.

In various embodiments, the step of correlating the first and second candidate breakpoints in step (c) comprises: identifying the first breakpoint from the RNA-SEQ detection step and the second breakpoint from the DNA-SEQ breakpoint detection steps that share a common location on the DNA reference sequence data set; and combining the identified first breakpoint and second breakpoint to generate a combined breakpoint list.

In various embodiments, the step of annotating the combined breakpoint list with biologically relevant information in step (d) comprises: determining a location of the combined breakpoint on a gene transcript to identify a gene fusion that is associated with each of the combined breakpoint; performing a transcript maturity analysis for the gene fusion to predict maturity of the gene fusion transcript; and annotating each of the combined breakpoint with information on the associated gene fusion and the predicted maturity of the gene fusion transcript.

In various embodiments, the step of annotating the combined breakpoint list with clinically relevant information in step (d) comprises: annotating the combined breakpoint list with information on whether the gene fusion is missing a conserved domain from a tumor suppressor gene or contains a conserved domain of an oncogene by comparing the gene fusion against a first database containing such information; and annotating the gene fusion data with information on a specific cancer therapy for a type of cancer that is associated with the gene fusion by comparing the gene fusion against second database containing such information. In various embodiments, step (b) is performed before or concurrently with step (a).

These and other advantages of the present invention will be apparent through references to the following description.

DETAILED DESCRIPTION

There are currently no products or methods that generate clinically relevant gene fusion data containing low false-positive gene fusion detections based on both a subject's DNA sequence information (DNA-SEQ) and RNA sequence information (RNA-SEQ) data sets.

The subject technology provides systems and methods for detecting gene fusion breakpoints and generate annotated gene fusion data from processing both a patient's DNA-SEQ data set and RNA-SEQ data set, thereby filtering out weak candidate gene fusions. The resultant annotated gene fusion data contains clinically relevant information and high specificity gene fusion identification (e.g., low false-positives) that can be used in clinical and/or R&D settings.

Advantageously, the subject technology helps a user to detect gene fusions with high specificity (e.g., low false-positives) based on a patient's DNA-SEQ and RNA-SEQ data sets, where the gene fusion data is annotated with information that is relevant for clinical and/or R&D application.

Figure 1:
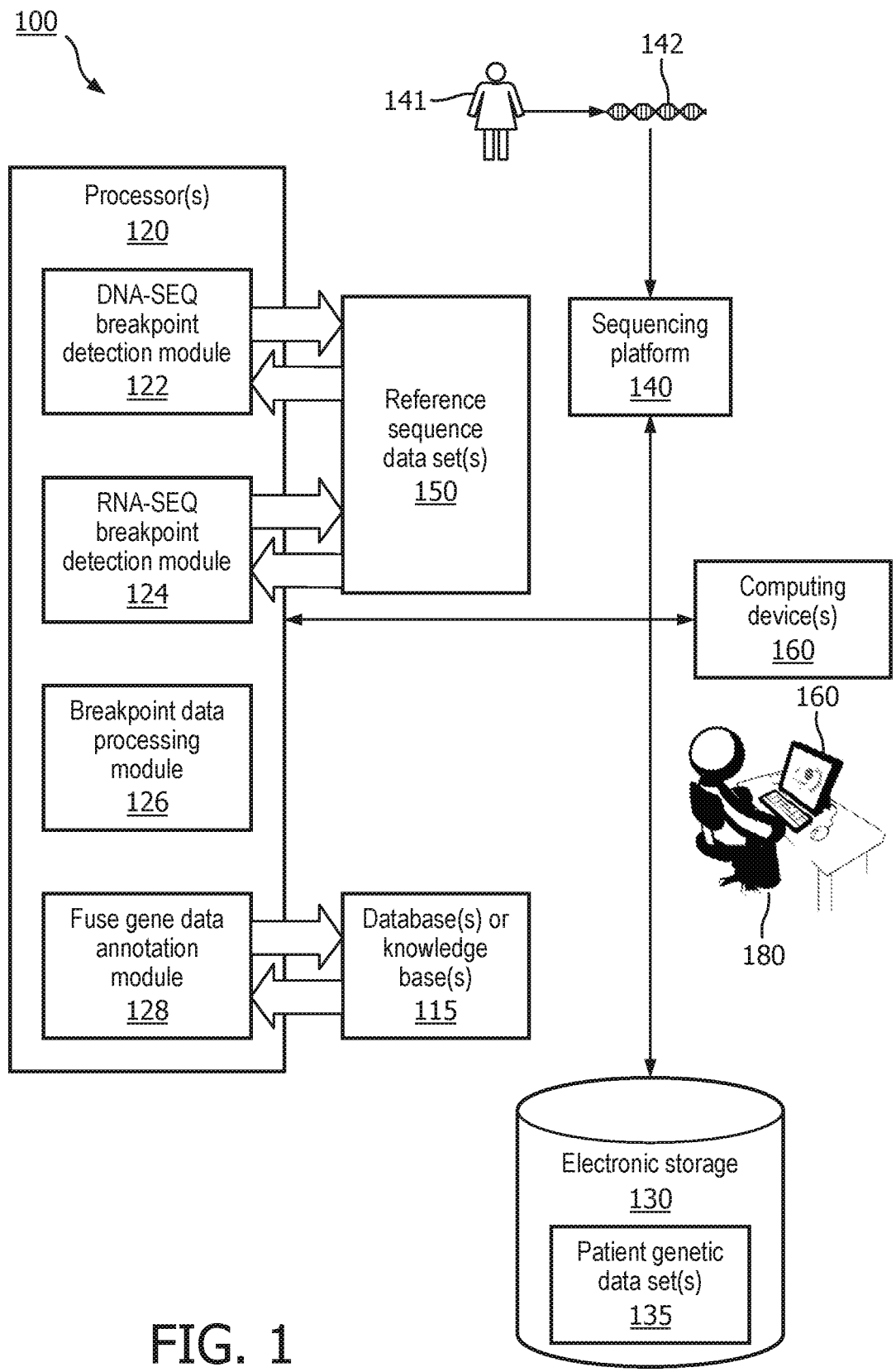
FIG. 1 illustrates a system for detecting gene fusions, according to invention principles.

FIG. 1 illustrates a system 100 configured to facilitate detection of gene fusion breakpoints accordance with one or more embodiments. In some embodiments, system 100 comprises one or more computing devices 160, one or more processors 120, electronic storage 130, sequencing platforms 140, and/or other components. Computing devices 160 can be configured to provide an interface between user 180 and system 100. Computing devices 160 can also be configured to provide information to user 180, receive information from user 180, and/or solicit an input (e.g., by prompting user 180 to provide an input) from user 180. Computing devices 160 include a user interface and/or other components. The user interface may include a graphical user interface configured to present views and/or fields configured to present information related to detected gene fusion from a patient genetic data 135 and/or annotated information associated with the detected gene fusion, such as clinically and/or biologically relevant information. In some embodiments, the user interface includes a plurality of separate interfaces associated with, for example, a plurality of computing devices 160, processors 120, and/or other components of system 100. Examples of user 180 includes healthcare providers (e.g., oncologist or clinical laboratory technician), researchers and developers of cancer diagnostics and/or therapy, patients, and/or a person who may benefit from the information provided by the system 100.

In some embodiments, one or more computing devices 160 are configured to provide a user interface, processing capabilities, databases, and/or electronic storage to system 100. As such, computing devices 160 may include processors 120, electronic storage 130, sequencing platform 140, and/or other components of system 100. In some embodiments, computing devices 160 are connected to a network (e.g., the Internet). In some embodiments, computing devices 160 do not include processor 120, electronic storage 130, sequencing platform 140, and/or other components of system 100, but instead communicate with these components via the network. The connection to the network may be wireless or wired. For example, processor 120 may be located in a remote server and may wirelessly receive the patient genetic data 135 from sequencing platform 140, and/or cause display of the detected gene fusion and/or other relevant information via the user interface on a computing device 110. In some embodiments, computing devices 160 are laptops, desktop computers, smartphones, tablet computers, smart watches, and/or other computing devices.

Examples of interface devices suitable for inclusion in the user interface include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that computing devices 160 include a removable storage interface. In this example, information may be loaded into computing devices 160 from removable storage (e.g., a smart card, a flash drive, a removable disk) that enables users 180 to customize the implementation of computing devices 160. Other exemplary input devices and techniques adapted for use with computing devices 160 and/or the user interface include, but are not limited to, an RS-232 port, RF link, an IR link, a modem (telephone, cable, etc.) and/or other devices.

In some embodiments, electronic storage 130 comprises electronic storage media that electronically stores information. The electronic storage media of electronic storage 130 may comprise one or both of system storage that is provided integrally (i.e., substantially non-removable) with system 100 and/or removable storage that is removably connectable to system 100 via, for example, a port (e.g., a USB port, a firewire port, etc.) or a drive (e.g., a disk drive, etc.). Electronic storage 130 may be (in whole or in part) a separate component within system 100, or electronic storage 130 may be provided (in whole or in part) integrally with one or more other components of system 100 (e.g., a computing device 110, processor 120, etc.). In some embodiments, electronic storage 130 may be located in a server together with processor 120, in a server that is part of sequencing platform 140, in computing devices 160, and/or in other locations. Electronic storage 130 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 130 may store software algorithms, information obtained and/or determined by processor 120, information received via computing devices 160 and/or other external computing systems, information received from sequencing platform 140 (e.g., patient genetic data 135), information received from, and/or other information that enables system 100 to function as described herein. By way of a non-limiting example, electronic storage 130 may store the patient genetic data 135 obtained by DNA-SEQ breakpoint detection module 122 and/or RNA-SEQ breakpoint detection module 124, the statistical models and/or mathematical formulae used by breakpoint data processing module 126, the gene fusion and associated information determined by gene fusion data annotation module 128, reference sequence data sets 150, databases or knowledge bases 115, and/or other information.

In some embodiments, sequencing platform 140 can include Next Generation Sequencing (NGS) platforms that can, for example, provide whole genome sequencing, targeted genome sequencing, whole-transcriptome sequencing, gene expression profiling, and or other genetic data. Sequencing platform 140 may accept genetic material 142 (e.g., genomic DNA and/or complementary DNA derived from mRNA) of patient 141 to produce patient genetic data 135. In some embodiments, genetic material 142 may be in a biological sample (e.g., tissue sample, blood sample, and/or tissue cell lysates) that contains a nucleic acid. In other embodiments, genetic material 142 may be in a processed form, for example, a NGS library comprising fragmented gDNA sample ligated to adapter molecules and immobilized on a substrate. In certain embodiments, sequencing platform 140 may be based on massive parallel sequencing technology, next generation sequencing technology, and/or other high-throughput nucleic acid sequencing technology. In some embodiments, the sequencing platform 140 may use pyrosequencing, reversible die terminator, oligonucleotide 8-mer chained ligation, native dNTPs proton detection, phospholinked fluorescent nucleotides, and/or any other methods of determining nucleotide sequences 135 of genetic material 142.

Sequencing platform 140 may be a separate system with its own computing components such as processor 120, electronic storage 130, computing devices 160, or other components of system 100. Alternatively, sequencing platform 140 may be integrated into an embodiment of the present technology. In addition, sequence platform 140 can include various specialized components for nucleic acid sequencing such as biological sample handling units, thermocycler units, optical detection units, and/or laser units. One skilled in the art would appreciate that sequencing platform 140 is not limited to those described in the present disclosure but can include any sequencing apparatus that can provide sequence information of nucleic acids. In some embodiments, the sequencing platform can rapidly and cost-effectively sequence a patient's genome and/or transcriptome, and such sequencing may be performed in a clinical and/or R&D setting, and/or by a service provider who provides sequencing services for hospitals, clinics, and/or research laboratories.

Sequencing platform 140 may access external sources of information (e.g., databases, websites, etc.), external entities participating with system 100, one or more servers outside of system 100, a network (e.g., the Internet), electronic storage, equipment related to Wi-Fi technology, equipment related to Bluetooth® technology, data entry devices, and/or other resources.

Processor 120 can be configured to provide information processing capabilities in system 100. As such, processor 120 may comprise one or more of a digital processor, an analog processor, a digital circuit designed to process information, an analog circuit designed to process information, a state machine, and/or other mechanisms for electronically processing information. Although processor 120 is shown in FIG. 1 as a single entity, this is for illustrative purposes only. In some embodiments, processor 120 may comprise a plurality of processing units. These processing units may be physically located within the same device (e.g., a server), or processor 120 may represent processing functionality of a plurality of devices operating in coordination (e.g., one or more servers, computing devices 160, devices that are part of sequencing platform 140, electronic storage 130, and/or other devices).

In some embodiments, processor 120, sequencing platform 140, computing devices 160, electronic storage 130, databases or knowledge bases 115, and other computing components of system 100 are part of a healthcare facility, a clinical laboratory, a genetic testing facility, and/or a service provider that provides gene sequence data analysis service to such parties. It will be appreciated that the above embodiments are not intended to be limiting, and that the scope of this disclosure includes embodiments in which these components may be operatively separately and linked via a communication media such as the internet and/or other network connections. In some embodiments, processor 120 is configured to communicate with sequencing platform 140, computing devices 160, electronic storage 130, databases or knowledge bases 115, the systems that are part of a client/server architecture, a peer-to-peer architecture, social media platform, and/or other architectures.

It should be appreciated that although components 122, 124, 126, and 128, are illustrated in FIG. 1 as being co-located within a single processing unit, in embodiments in which processor 120 comprises multiple processing units, one or more of components 122, 124, 126, and/or 128 may be located remotely from the other components. The description of the functionality provided by different components 122, 124, 126, and/or 128 described below is for illustrative purposes, and is not intended to be limiting, as any of components 122, 124, 126, and/or 128 may provide more or less functionality than is described. For example, one or more of components 122, 124, 126, and/or 128 may be eliminated, and some or all of its functionality may be provided by other components 122, 124, 126, and/or 128. As another example, processor 120 may be configured to execute one or more additional components that may perform some or all of the functionality attributed below to one of components 122, 124, 126, and/or 128.

It should also be appreciated that although reference sequence data 150 is illustrated in FIG. 1 as being a single unit that is external to processors 120, electronic data storage 130, sequencing platform 140, and/or computing devices 160, reference sequence data 150 can be processed by processors 120 and co-located within electronic storage 130, sequencing platform 140, and/or computing devices 160. Reference sequence data 150 can also be remotely located, for example on an external sever (e.g., publicly available database or subscription-based database, accessible via the internet) and/or may comprise two or more distinct data sets (e.g., a genomic DNA reference data, a transcriptome reference data, and/or a RNA transcript reference data) that may be part of a same database or separate databases. For example, each of the DNA-SEQ breakpoint detection module 122 and RNA-SEQ breakpoint detection module 124 can each be associated with separate reference sequence data 150.

Figure 6:
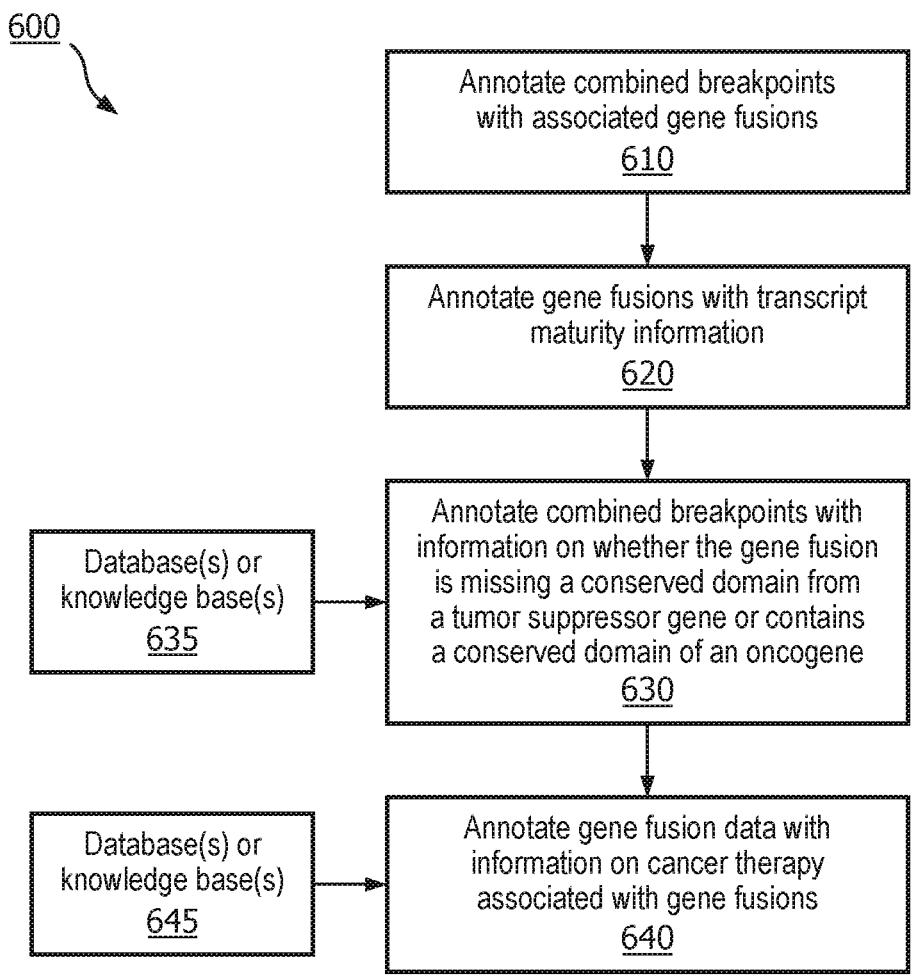
FIG. 6 illustrates the combined breakpoints annotation step of FIG. 2, according to invention principles.

Similarly, it should also be appreciated that although database or knowledge base 115 is illustrated in FIG. 1 as being a single unit that is external to processors 120, electronic data storage 130, sequencing platform 140, and/or computing devices 160, database or knowledge base 115 can be processed by processors 120 and co-located within electronic storage 130, sequencing platform 140, and/or computing devices 160. Database or knowledge base 115 can also be remotely located, for example on an external sever (e.g., publicly available or subscription-based database, accessible via the internet). In addition, as illustrated in FIG. 6, database or knowledgebase 115 can include multiple discrete databases and/or knowledge bases 635, 645.

As used herein, patient 141 can include a human subject or a non-human subject. Patient 141 can also refer to biopsy samples, bodily fluid samples, and/or other biological samples from a human subject or a non-human subject. In other embodiments, patient 141 can also include cell lines (e.g., immortalized cell lines), and/or primary tissue culture that are sourced and/or derived from a human subject or a non-human subject.

As used herein, nucleic acid 142 can include ribonucleic acid (RNA) or deoxyribonucleic acid (DNA) obtained from a patient or copies of such RNA or DNA (e.g., cDNA that is reverse-transcribed from messenger RNA (mRNA) and/or pre-messenger RNA (pre-mRNA); amplified DNA produced by polymerase chain reaction from a patient's genomic DNA or cDNA.

As used herein, user 180 can include medical professionals, such as oncologists, pathologists, laboratory technicians, and/or cancer genetic test providers, who wants to access patient's gene fusion data for cancer diagnosis and/or treatment purposes (e.g., tailoring personalized treatment). User 180 can also refer to researchers, scientists, and/or developers of cancer diagnosis and/or treatment technology, who want to, for example, use a patient's gene fusion data for designing, testing, refining, and/or validating new cancer diagnosis (e.g., cancer genetic test) and/or treatment technologies. User 180 can further include patients (e.g., cancer patients or those being screened for cancer) who may receive the user's own gene fusion data (e.g., such gene fusion data information being provided by a service provider), that also contains relevant clinical information and/or treatment suggestions. User 180 can sto; further also include any person that may benefit from accessing a patient's gene fusion data.

As illustrated in FIG. 1, in some embodiments, data processing system 100 for providing clinically relevant gene fusion breakpoints and associated information may include processor 120 being operable to (a) detect, using DNA-SEQ breakpoint detection module 122, a first set of candidate breakpoints based on DNA-SEQ data set 135 by comparing DNA-SEQ data set 135 to DNA reference sequence data set 150; (b) detect, using RNA-SEQ breakpoint detection module 124, a second set of candidate breakpoints based on RNA-SEQ data set 135 by comparing RNA-SEQ data set 135 to both DNA reference sequence data set 150 and RNA reference data set 150; (c) correlate, using breakpoint data processing module 126, the first and second sets of candidate breakpoints to generate a combined breakpoint list, characterized by a higher threshold specificity; (d) annotate, using gene fusion data annotation module 128, the combined breakpoint list with biologically and clinically relevant information to generate an annotated gene fusion data set. The modules listed herein are configured to work together to provide user 180 with a high specificity gene fusion data set that contains a lower false-positive breakpoint detection rate compared to a false-positive detection rate in the absence of the correlation in step (c). The gene fusion data set is annotated with clinically relevant information such that user 180 can use the gene fusion data set for making clinical and/or cancer R&D decisions. One skilled in the art would appreciate that two or more of the above processes listed can be performed concurrently and/or contemporaneously, and/or the order with which the above processes are performed can be changed. For example, DNA-SEQ breakpoint detection module 112 can detect a first set of candidate breakpoints concurrently with RNA-SEQ breakpoint detection module 124 detecting a second set of candidate breakpoints.

Figure 2:
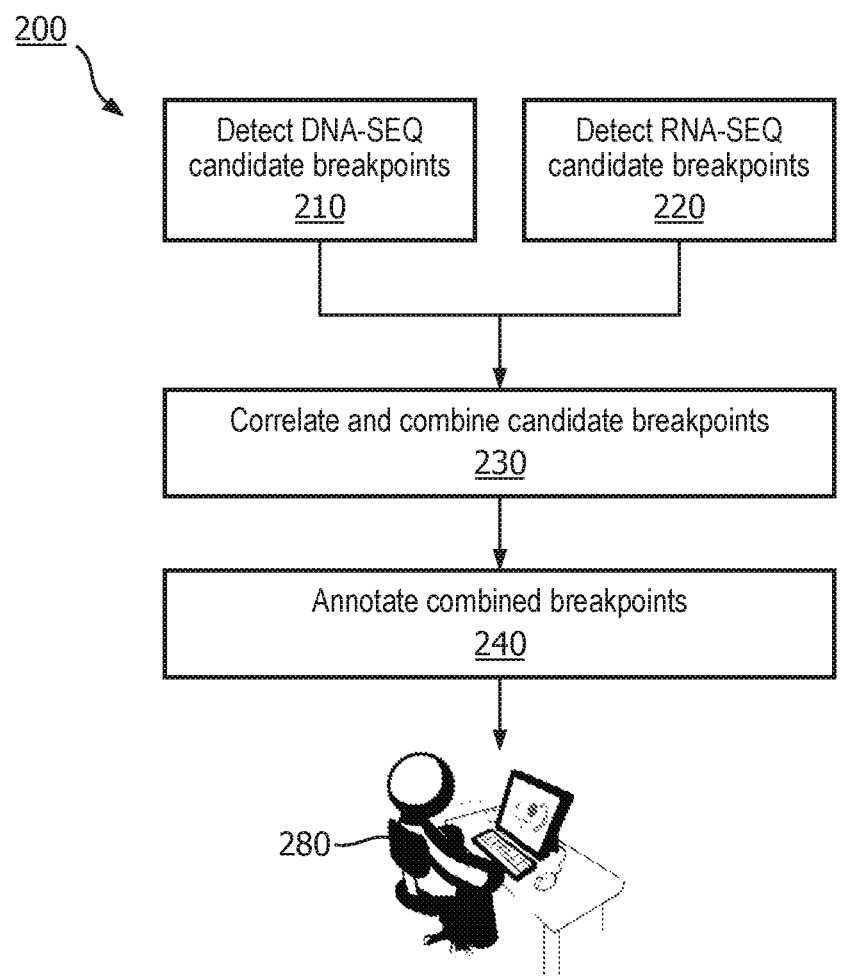
FIG. 2 illustrates a method for detecting gene fusions, according to invention principles.

FIG. 2 is a flow diagram of method 200 that may be used by embodiments described herein. Method 200 may be performed by a data processing system (i.e., system 100) for detecting and processing gene fusion from patient genetic data 135. Several non-limiting embodiments of system 100 that may use method 200 is described elsewhere in this application. The operations of method 200 presented below are intended to be illustrative. In one exemplary embodiment with respect to a computer-implemented method 200 for providing clinically relevant gene fusion breakpoints and associated information, system 100 is used to carry out the following steps: (a) detecting a first candidate breakpoint based on a DNA-SEQ data set 210 by comparing the DNA-SEQ data set to a DNA reference sequence data; (b) detecting a second candidate breakpoint based on a RNA-SEQ data set 220 by comparing the RNA-SEQ data set to both a DNA reference sequence data set and a RNA reference data set; (c) correlating the first and second candidate breakpoints 230 to generate a combined breakpoint list, characterized by a higher threshold specificity; (d) annotating the combined breakpoint list with biologically and clinically relevant information 240 to generate an annotated gene fusion data set, wherein the combined breakpoint list of step (c) has a lower false-positive breakpoint detection rate compared to a false-positive breakpoint detection rate in the absence of the correlation in step (c), and wherein the annotated gene fusion data set is suitable for being used for having a clinical decision made.

Figures 3A, 3B:
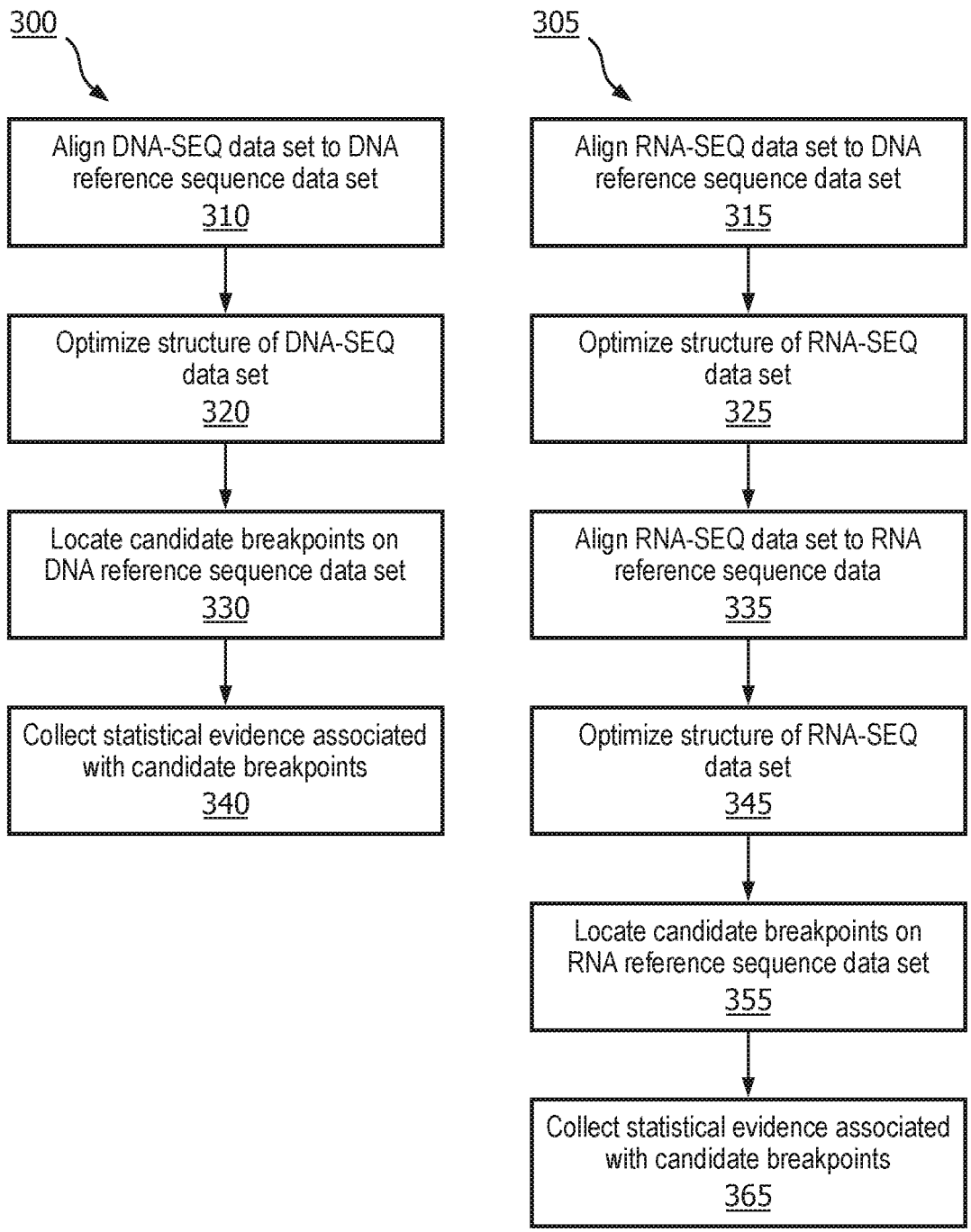
FIG. 3A illustrates the DNA-SEQ candidate breakpoints detection step of FIG. 2, according to invention principles.
FIG. 3B illustrates the RNA-SEQ candidate breakpoints detection step of FIG. 2, according to invention principles.

FIG. 3A is a flow diagram illustrating processes that are included in an embodiment of the DNA-SEQ breakpoint detection step 300, 210. As illustrated in FIG. 3A, in some embodiments, DNA-SEQ breakpoint detection module 122 is configured to detect the DNA-SEQ candidate breakpoints by comparing DNA-SEQ data set 135 to DNA reference sequence data set 150. More specifically, DNA-SEQ breakpoint detection module 122 can perform the following steps: optimizing structure of DNA-SEQ data set 310 by sorting, removing duplicates from, and indexing the DNA-SEQ data set; aligning the DNA-SEQ data set with the DNA reference sequence data set 320; determining locations of candidate breakpoints relative to the DNA reference sequence data set 330; and collecting statistical evidence associated with the candidate breakpoints 340. One skilled in the art would appreciate that two or more of the above processes 310, 320, 330, 340 listed can be performed in parallel and/or concurrently, and the order with which the above processes are performed can be changed.

In some embodiments, DNA-SEQ breakpoint detection module 122 can obtain patient genetic data 135 (e.g., a patient's genomic DNA sequence information 135) in one of a variety of formats (e.g., FASTA, FASTQ, and/or other proprietary format), depending, for example, on sequencing platform 140 that is used to generate the patient genetic data 135. Thus, the process of obtaining patient genetic data 135 from sequencing platform 140 can include standardization of the read format in such a way that patient genetic data 135 can be used for further processing and analysis described herein. One non-limiting example of standardizing sequence format is adjusting quality score format of patient genetic data 135.

In some embodiments, reference sequence data 150 can be a publicly available reference genomic sequence information such as GRCh38 or other similar reference genome. Reference sequence data 150 may also be a proprietary/private sequence data that is generated and/or maintained by user 180 or a third party.

In some embodiments, structure of patient genetic data 135 can be optimized 310 to enhanced (e.g., accelerated or more efficient) retrieval of patient genetic data 135. For example, patient genetic data 135 may be sorted and grouped in a particular order, duplicate sequence information is removed, and/or a sequence file index is created.

In some embodiments, the candidate breakpoints can be identified by first identifying suspect breakpoints (e.g., abnormal regions where higher than normal levels of abnormally mapped reads are identified), and then validating suspect breakpoints by checking sequence reads of both ends of the suspect breakpoints.

In some embodiments, the statistical evidence for the candidate breakpoints can be information regarding number of support reads and total reads located on top of both ends of the breakpoints. Such statistical evidence can be summarized and mapping information for these reads can be stored (e.g., annotated or linked to the candidate breakpoint data).

FIG. 3B is a flow diagram illustrating processes that are included in an embodiment of RNA-SEQ breakpoint detection step 305, 220. As illustrated in FIG. 3B, in some embodiments, RNA-SEQ breakpoint detection module 124 is configured to detect the RNA-SEQ candidate breakpoints by comparing RNA-SEQ data set 135 to both DNA reference sequence data set 150 and RNA reference sequence data set 150. More specifically, RNA-SEQ breakpoint detection module 124 can perform the following steps: aligning the RNA-SEQ data set with a DNA reference sequence data set 315; optimizing structure of the RNA-SEQ data set 325 by sorting and removing duplicates from the RNA-SEQ data set; aligning the RNA-SEQ data set with the RNA reference sequence data set 335; optimizing structure of the RNA-SEQ data set 345 by sorting and removing duplicates from the RNA-SEQ data set; determining locations of candidate breakpoints relative to the RNA reference sequence data set 355; and collecting statistical evidence associated with the candidate breakpoints 365. One skilled in the art would appreciate that two or more of the above processes 315, 325, 335, 345, 355, 365 listed can be performed in parallel and/or concurrently, and the order with which the above processes are performed can be changed.

In some embodiments, patient genetic data 135 that is obtained by RNA-SEQ breakpoint detection module 124 is patient's 141 mRNA sequence information 135 and/or cDNA sequence information 135. RNA sequence information 135 can be in one of a variety of formats, depending, for example, on sequencing platform 140 that is used. Thus, the process of obtaining patient genetic data 135 can include standardization of the read format in such a way that patient genetic data 135 can be used for further processing and analysis described herein. One non-limiting example of standardizing sequence format is adjusting quality score format of patient genetic data 135.

In some embodiments, reference sequence data 150 for RNA-SEQ breakpoint detection module 124 can comprise reference DNA genomic sequences, reference mRNA transcript sequences and/or reference transcriptome sequences. Such reference sequence data 150 can be obtained from a publicly available database and/or a proprietary/private sequence data that is created and/or maintained by user 180 or a third party. In some embodiments, the candidate breakpoints can be identified by first estimating insert size according to normally mapped data, and then identifying abnormally mapped parts, whose reads could not be mapped onto a same transcript.

Figure 4:
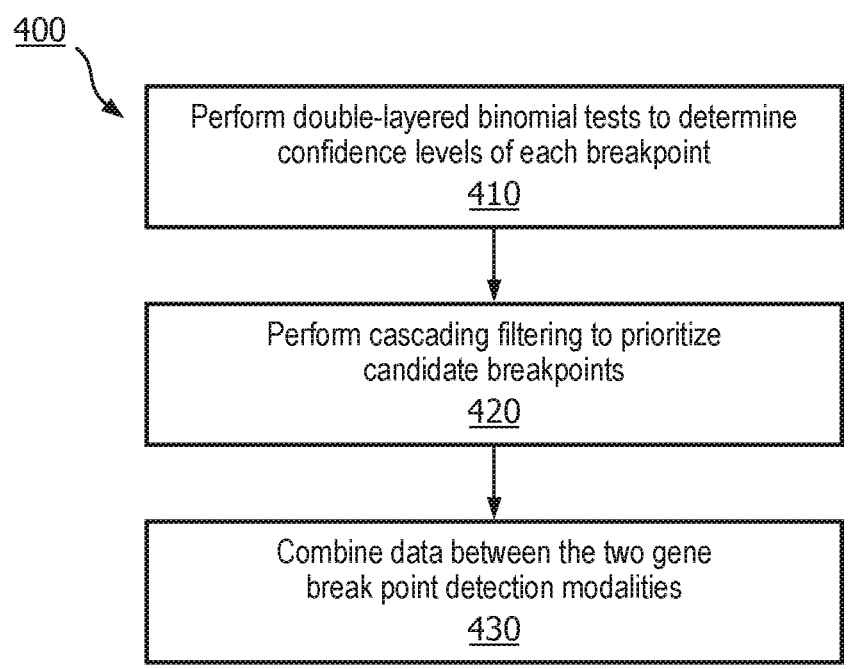
FIG. 4 illustrates the candidate breakpoints correlation and combination step of FIG. 2, according to invention principles.

FIG. 4 is a flow diagram illustrating processes that are included in an embodiment of breakpoint data processing step 400, 230. As shown in FIG. 4, in some embodiments, breakpoint data processing module 126 is configured to correlate and combine the candidate breakpoints from DNA-SEQ detection step 122 and RNA-SEQ detection step 124 by performing the following: (1) calculating a confidence level for each breakpoint (for example by using double layered binomial test) 410; (2) performing a cascading filtering to prioritize the breakpoints 420; and (3) combining the breakpoints that are detected from RNA-SEQ and DNA-SEQ breakpoint detection steps 430. One skilled in the art would appreciate that two or more of the above processes 410, 420, 430 listed can be performed in parallel and/or concurrently, and the order with which the above processes are performed can be changed.

In some embodiments, confidence levels of each of the candidate breakpoints are calculated using supporting evidence for the candidate breakpoints. In some embodiments, the supporting evidence can include spanning reads and/or junction reads (i.e. the more spanning reads and/or junction reads for a given sequence segment indicating higher level of supporting evidence). In other embodiments, a double-layered scoring model can be used to evaluate a confidence level for each candidate breakpoint from a single modality (i.e., either from a DNA-SEQ or RNA-SEQ source), where each of the layers correspond to each side of a breakpoint. Various statistical methods can be used to determine a statistical significance of a breakpoint given the evidence from the sequencing data. In some embodiments, a binomial test can be used to determine the confidence level. For example, assuming on top of the $i^{th}$ (1=1 or 2) end of a candidate breakpoint, there are $n_i$ supporting reads and $m_i$ reads in total. Moreover, in $n_i$ and $m_i$, there are $l_i$ and $k_i$ pair-end reads while the rest are junction reads with anchor lengths of no less than a threshold $\Omega$. Further assuming the mapping error rate for a sequence with length no less than $\Omega$ follows a binomial distribution with a prior probability as p, the probability to observe r miss-mapped reads out of total n reads would be $$P(X = r) = \binom{n}{r} p^r (1-p)^{n-r},$$

$$\text{where } \binom{n}{r} = n!/(r!(n-r)!).$$

Therefore, the statistical significance to observe $n_i$ supporting reads out of $m_i$ reads would be $$SS_i = 1 - \sum_{r=1}^{n_i-1} \left( \binom{m_i}{r} p^r (1-p)^{m_i-r} \right).$$

Taking evidences from both ends for a candidate into consideration, statistical significance for a breakpoint can be calculated by calculating the geometric mean of the statistical significance of each layer by calculating $SS_b = (\Pi_{i=1}^{2} SS_i)^{1/2}$. To select confident calls by $SS_b$, a threshold of $\delta/w$ is chosen, with a predefined statistical significance $\delta$ (e.g. 0.05) after family-wise error correction by the size of whole gene covered regions, w. This method will be used in embodiments where only single modality is used for detecting fusions, i.e. either RNA-SEQ or DNA-SEQ.

Figure 5:
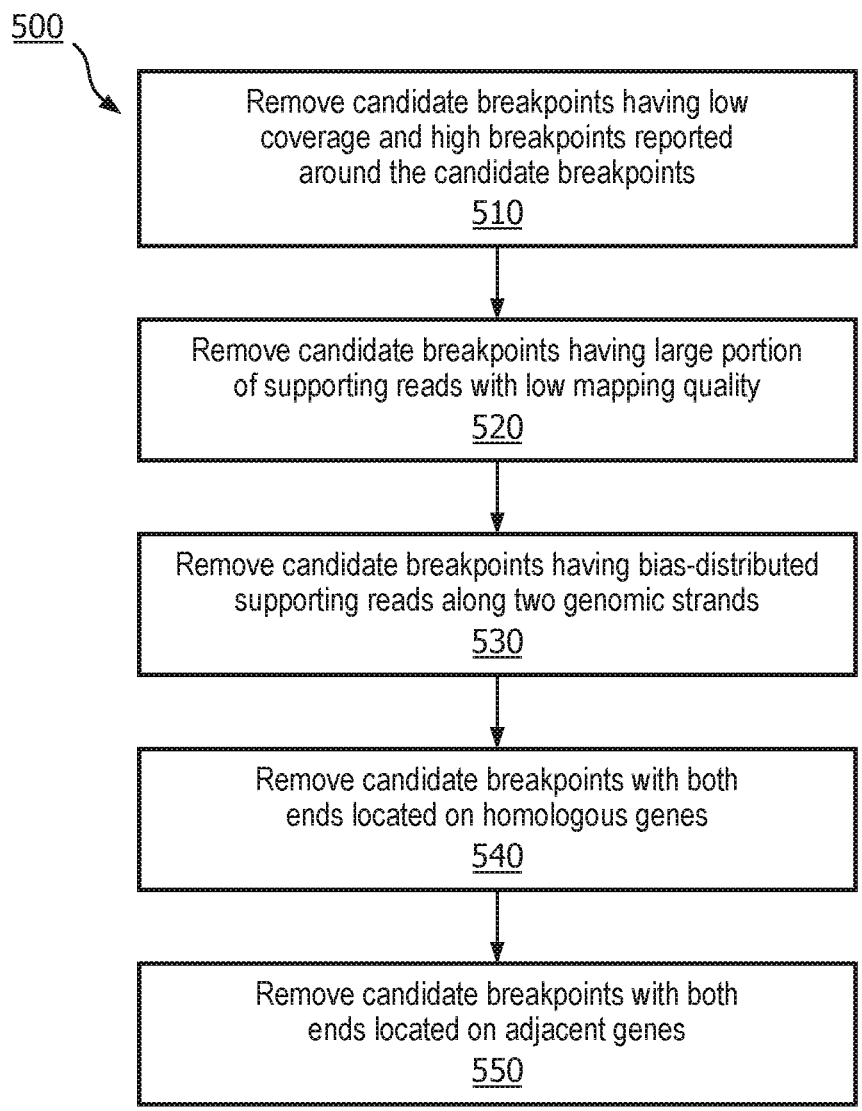
FIG. 5 illustrates the cascading filtering step of FIG. 4, according to invention principles.

FIG. 5 is a flow diagram illustrating processes that are included in an embodiment of gene fusion annotation step 500, 240 of method 200 illustrated in FIG. 2, illustrating processes that are included in cascading filtering step 420, 500. As shown in FIG. 5, in some embodiments, cascading filtering 500 can include various processes for removing weak candidate breakpoints (e.g., candidate breakpoints that are likely to be false-positives or identified as a breakpoint when that is not the case), such as (1) removing candidate breakpoints with many other mutations/breakpoints reported around if the coverage is low 510; (2) removing candidate breakpoints with large portion of supporting reads found with very low mapping quality 520; (3) removing candidate breakpoints with supporting read bias-distributed along two genomic strands 530; (4) removing candidate breakpoints with both ends located on homologous genes 540; and (5) removing candidate breakpoints with both ends located on adjacent genes 550. One skilled in the art would appreciate that terms such as "low" or "very low" used to describe certain aspects of the data are context specific, such that a skilled user can determine, from experience, sequencing platform used, and/or other factors, determine a threshold or range for determining what is "low" or "very low". One skilled in the art would appreciate that two or more of the above processes 510, 520, 530, 540, 550 listed can be performed in parallel and/or concurrently, and the order with which the above processes are performed can be changed.

In some embodiments, breakpoint data processing module 126 is configured to correlate the first and second candidate breakpoints by: identifying the first breakpoint from the RNA-SEQ detection step and the second breakpoint from the DNA-SEQ breakpoint detection steps that share a common location on a chromosome; and combining the identified first breakpoint and second breakpoint to generate a combined breakpoint list. For example, if a breakpoint detected as chr1:35652550→chrX:48891800 by DNA-SEQ, and the breakpoint is also detected by RNA-SEQ with as chr1:35652602→chrX:48891766 (or described as the 3 prime of 9th exon of NM_005066 is fused with 3 prime of 6th exon of NM_006521), such information pair will be considered as a match, since the former location could be matched on the latter after transcription. Each of the breakpoints that are identified as sharing common location on a chromosome can be combined and given a statistical significance calculated from the geometric average of the statistical significance calculated from DNA-SEQ and RNA-SEQ breakpoint detection steps 210, 220.

FIG. 6 is a flow diagram illustrating processes that are included in an embodiment of combined breakpoints annotation step 240, 600. As shown in FIG. 6, in some embodiments, gene fusion data annotation module 128 is configured to annotate the combined breakpoint list with biologically relevant information by: determining locations of the combined breakpoints on a gene transcript to identify gene fusions that are associated with each of the combined breakpoints; performing a transcript maturity analysis for the gene fusions to predict maturity of the gene fusion transcripts; and annotating each of the combined breakpoints with information on the associated gene fusions 610 and the predicted maturity of the gene fusion transcripts 620. Gene fusion data annotation module 128 is configured to further annotate the combined breakpoints with clinically relevant information by: annotating the combined breakpoint list with information on whether the gene fusions are missing conserved domains from tumor suppressor genes or contains conserved domains of cancer-type specific oncogenes by comparing the gene fusion transcripts against a database containing such information 630; and annotating the gene fusion data with information on specific cancer therapies for types of cancer that are associated with the gene fusions by comparing the gene fusions against a database containing such information 640.

In some embodiments, transcript maturity analysis 620 predicts whether the detected gene fusions will result in immature (and/or truncated) transcripts that are missing certain sequences (e.g., does not contain transcript sequence due to immature transcripts) corresponding to cancer-relevant genes (e.g., conserved regions of tumor suppressor genes). In other embodiments, the transcript maturity analysis predicts whether the detected gene fusions will result in mature transcript that includes sequences corresponding to cancer-relevant genes (e.g., conserved regions of a cancer type specific oncogene). Information regarding gene fusion transcripts containing and/or missing cancer-relevant genes (e.g., missing tumor suppressor gene conserved sequences and/or containing oncogene conserved sequences) can be annotated to the associated gene fusion. Other information associated with breakpoints that has clinical relevance can also be annotated to the gene fusion data.

Database or knowledge base 115, 635 containing cancer-type oncogene and tumor suppressor gene information can be created and maintained the user, a third-party service provider, and/or be from a publicly available database. In some embodiments, the gene fusion data can be annotated with specific cancer types that the gene fusion is associated with. For example, gene fusion data can be compared to a database containing information on associations of gene fusions to specific cancer types. Database or knowledge base 115, 635 containing information on associations of gene fusions and cancer types can be created and maintained the user, a third-party service provider, and/or be from a publicly available database. Non-limiting examples of publicly available database that can be used is The Cancer Genome Atlas (TCGA) or the Catalogue of Somatic Mutations in Cancer (COSMIC). Database or knowledge base 115, 635 can also be internally generated and/or proprietary products that are generated and/or maintained by the user or a third party (e.g., a database subscription service).

In some embodiments, the gene fusion data can be annotated with therapies (e.g., FDA approved drugs) that target types of cancers associated with gene fusions. Database or knowledge base 115, 645 containing cancer therapies that are specific for cancer types associated with specific gene fusions can be created and maintained the user, a third-party service provider, and/or be from a publicly available database.

The annotated gene fusion data may be provided or otherwise made available to user 180 via computing devices 160 (e.g., using a graphic user interphase, a printer, and/or a screen display). Generation, accessing, processing, providing, and/or otherwise handling of patient genetic data 135 may require a high level of privacy protection. For example, the present invention may be used by a sequencing service laboratory with a Clinical Laboratory Improvement Amendment (CLIA) certification, or have reached a data security agreement with patients and/or their delegates. The present invention can also be used and/or handled by patients themselves.

The annotated gene fusion data will be used by users 180 in making various decisions. In one embodiment, user 180 is a clinician (e.g., medical oncologist) and the annotated gene fusion data is used in making clinical decisions (e.g., diagnosis of a disease, decisions regarding treatment of a disease) regarding the patient whose sequence information the annotated gene fusion data is generated from. In another embodiment, user 180 is a cancer genetic test developer and the annotated gene fusion data is used in planning, running, validating, conducting, and/or otherwise making decisions associated with research and development of cancer genetic test. In yet another embodiment, user 180 is patient 141 (e.g., cancer patient, or someone who is being screened for cancer/tumor) and the annotated gene fusion data are used in making clinical decisions, together with a medical professional. In other embodiments, the annotated gene fusion data can be used as an input data for another system, such as patient records management system of a healthcare facility. The annotated gene fusion data can contain at least one of, some of, or all of the following information: (1) exact location of breakpoints on human reference genome and transcriptome (2) statistical significance from each single modality (DNA/RNA) and their combination, biological consequence (e.g., immature or mature fused transcripts), clinical relevance (types of cancer that is associated with the gene fusion), and potential treatment/therapy.

The following examples are illustrative and not restrictive. Many variations of the technology will become apparent to those of skill in the art upon review of this disclosure. The scope of the technology should, therefore, be determined, not with reference to the examples, but instead should be determined with reference to the appended claims along with their full scope of equivalents.

EXAMPLES

Example 1: Use of the Technology by a Medical Professional

A medical oncologist, A, may want to find a suitable targeted therapy with low toxicity for his patient, B, with late-stage lung cancer. A will order whole genome DNA sequencing and whole transcriptome sequencing for B from CLIA lab within the hospital for investigating B's mutation landscape. The patient genetic data generated will be input of a computer system comprising an embodiment of the present technology. The computer system will handle sequencing data alignment to human reference genome and transcriptome in parallel, detecting/annotating breakpoints, false-positive filtering, evidence combining and statistical significance calculation, gene fusion reporting and clinical evidence aggregation. In the report that will be generated, potential fusions will be recorded with exact breakpoint on human reference genome and transcriptome, statistical significance from each single modality (DNA/RNA) and their combination, biological consequence (with immature/mature fused transcripts), clinical relevance and potential treatment/therapy. In such scenario, confident fusions will be prioritized with (1) if potential treatment/therapy exist; (2) if clinical relevance indicate this is a cancer driver. E.g. if the patient bares both EML4-ALK and CCD6-RET fusions, EML4-ALK will be put on top since two drugs are available for this fusion as Ceritinib (Zykadia®) and Crizotinib (Xalkori®). The results will be provided to the user, and the user will use the information that is provided in making clinical decisions.

Example 2: Use of the Technology by a Researcher and/or Developer of Cancer Diagnosis or Treatment Technology A genetic test developer, C, developing a companion test for a pharmaceutical company's pre-drug for cancer, may wish to find biomarkers to predict if the patient will be resistant to a compound. C will want to explore the potential of fusions to work as such biomarker. After achieving a user license for platform-independent version of this software, C will set up the software onto his own HPC (High Performance Computing environment) and start to handle his private NGS data from hundreds of patients. For each sample, a confident gene fusion list will be reported from the software. After integrating all these fusion lists together, correlation between recurrent fusions and response of patients to the compound will be calculated for evaluating if some fusions are potential to be such biomarker. Significant findings will be validated and developed into a new genetic test.

Example 3: Use of an Embodiment of the Technology by a Patient

A cancer patient, D, may want to scan his DNA-SEQ/RNA-SEQ data for confident mutations, including fusion, for tracing a suitable treatment for himself. D will register himself on a service provider's private cloud and will upload his sequencing data plus his basic disease information. The service provider will send him back a report including a confident gene fusion list and clinical evidence aggregated around the gene fusion list. Then D will put the report on his social network webpage and D will discuss with doctors and his care providers about the most suitable treatment for his case.

What is claimed is:

1. A computer-implemented method for providing clinically relevant gene fusion breakpoints and associated information, the method being based on disparate sequencing data sets and comprising:
    (a) detecting a first candidate breakpoint based on a DNA-SEQ data set by comparing the DNA-SEQ data set to a DNA reference sequence data set;
    (b) detecting a second candidate breakpoint based on a RNA-SEQ data set by comparing the RNA-SEQ data set to both a DNA reference sequence data set and a RNA reference data set;
    (c) correlating the first and second candidate breakpoints to generate a combined breakpoint list, characterized by a higher threshold specificity;
    (d) annotating the combined breakpoint list with biologically and clinically relevant information to generate an annotated gene fusion data set,
    wherein the combined breakpoint list of step (c) has a lower false-positive breakpoint detection rate compared to a false-positive breakpoint detection rate in the absence of the correlation in step (c),
    wherein the annotated gene fusion data set is suitable for being used for having a clinical decision made, and
    wherein the DNA-SEQ data set and the RNA-SEQ data set are each obtained from a different sequencing platform and standardized into a common read format before detecting the first or second candidate breakpoints.

2. The method of claim 1, wherein the step of comparing the DNA-SEQ data set to DNA reference sequence data set in step (a) comprises:
    optimizing structure of the DNA-SEQ data set by sorting, removing duplicates from, and indexing the DNA-SEQ data set;
    aligning the DNA-SEQ data set with the DNA reference sequence data set;
    determining a location of the candidate breakpoint relative to the DNA reference sequence data set; and
    collecting statistical evidence associated with the candidate breakpoint.

3. The method of claim 1, wherein the step of comparing the RNA-SEQ data set to both DNA reference sequence data set and RNA reference sequence data set in step (b) comprises:
    aligning the RNA-SEQ data set with the DNA reference sequence data set;
    optimizing structure of the RNA-SEQ data set by sorting and removing duplicates from the RNA-SEQ data set;
    aligning the RNA-SEQ data set with the RNA reference sequence data set;
    optimizing structure of the RNA-SEQ data set by sorting and removing duplicates from the RNA-SEQ data set;
    determining a location of the candidate breakpoint relative to the RNA reference sequence data set;
    determining a location of the candidate breakpoint relative to the DNA reference sequence data set; and
    collecting statistical evidence associated with the candidate breakpoint.

4. The method of claim 1, wherein the step of correlating the first and second candidate breakpoints in step (c) comprises performing a cascading filtering, the cascading filtering comprising:
    removing the candidate breakpoint having low coverage and high breakpoints reported around the candidate breakpoint;
    removing the candidate breakpoint having large portion of supporting reads with low mapping quality;
    removing the candidate breakpoint having bias-distributed supporting read along two genomic strands;
    removing the candidate breakpoint with both ends located on homologous genes; and
    removing the candidate breakpoint with both ends located on adjacent genes.

5. The method of claim 1, wherein the step of correlating the first and second candidate breakpoints in step (c) comprises:
    identifying the first breakpoint from the DNA-SEQ breakpoint detection step and the second breakpoint from the RNA-SEQ breakpoint detection steps that share a common location on the DNA reference sequence data set; and
    combining the identified first breakpoint and second breakpoint to generate a combined breakpoint list.

6. The method of claim 1, wherein the step of annotating the combined breakpoint list with biologically relevant information in step (d) comprises:
    determining a location of the combined breakpoint on a gene transcript to identify a gene fusion that is associated with each of the combined breakpoint;
    performing a transcript maturity analysis for the gene fusion to predict maturity of the gene fusion; and
    annotating each of the combined breakpoint with information on the associated gene fusion and the predicted maturity of the gene fusion.

7. The method of claim 6, wherein the step of annotating the combined breakpoint list with clinically relevant information in step (d) comprises:
    annotating the combined breakpoint list with information on whether the gene fusion transcript is missing a conserved domain from a tumor suppressor gene or contains a conserved domain of an oncogene by comparing the gene fusion against a first database containing such information; and
    annotating the gene fusion data with information on a specific cancer therapy for a type of cancer that is associated with the gene fusion by comparing the gene fusion against second database containing such information.

8. The method of claim 1, wherein step (b) is performed before or concurrently with step (a).

9. A data processing system for providing clinically relevant gene fusion breakpoints and associated information, the system comprising:
- at least one memory operable to store a data repository;
- a DNA sequencing platform and an RNA sequencing platform communicatively coupled to the at least one memory, wherein the DNA sequencing platform and the RNA sequencing platform are different; and
- a processor communicatively coupled to the at least one memory, the processor being operable to:
  - (a) detect, using a DNA-SEQ breakpoint detection module, a first candidate breakpoint based on a DNA-SEQ data set by comparing the DNA-SEQ data set to a DNA reference sequence data set after standardizing the DNA-SEQ data set into a read format;
  - (b) detect, using a RNA-SEQ breakpoint detection module, a second candidate breakpoint based on a RNA-SEQ data set by comparing the RNA-SEQ data set to both a DNA reference sequence data set and a RNA reference data set after standardizing the RNA-SEQ data set into the read format;
  - (c) correlate, using a breakpoint data processing module, the first and second candidate breakpoints to generate a combined breakpoint list, characterized by a higher threshold specificity;
  - (d) annotate, using a gene fusion data annotation module, the combined breakpoint list with biologically and clinically relevant information to generate an annotated gene fusion data set,
  - wherein the combined breakpoint list of step (c) has a lower false-positive breakpoint detection rate compared to a false-positive breakpoint detection rate in the absence of the correlation in step (c), and
  - wherein the annotated gene fusion data set is suitable for being used for having a clinical decision made.

10. The system of claim 9, wherein the DNA-SEQ breakpoint detection module is configured to compare the DNA-SEQ data set to DNA reference sequence data set by:
- aligning the DNA-SEQ data set with the DNA reference sequence data set;
- optimizing structure of the DNA-SEQ data set by sorting, removing duplicates from, and indexing the DNA-SEQ data set;
- determining a location of the candidate breakpoint relative to the DNA reference sequence data set; and
- collecting statistical evidence associated with the candidate breakpoint.

11. The system of claim 9, wherein the RNA-SEQ breakpoint detection module is configured to compare the RNA-SEQ data set to both DNA reference sequence data set and RNA reference sequence data set by:
- aligning the RNA-SEQ data set with the DNA reference sequence data set;
- optimizing structure of the RNA-SEQ data set by sorting and removing duplicates from the RNA-SEQ data set;
- aligning the RNA-SEQ data set with the RNA reference sequence data set;
- optimizing structure of the RNA-SEQ data set by sorting and removing duplicates from the RNA-SEQ data set;
- determining a location of the candidate breakpoint relative to the RNA reference sequence data set; and
- collecting statistical evidence associated with the candidate breakpoint.

12. The system of claim 9, wherein the breakpoint data processing module is configured to correlate the first and second candidate breakpoints by performing a cascading filtering, the cascading filtering comprising:
- removing the candidate breakpoint having low coverage and high breakpoints reported around the candidate breakpoint;
- removing the candidate breakpoint having large portion of supporting reads with low mapping quality;
- removing the candidate breakpoint having bias-distributed supporting reads along two genomic strands;
- removing the candidate breakpoint with both ends located on homologous genes; and
- removing the candidate breakpoint with both ends located on adjacent genes.

13. The system of claim 9, wherein the breakpoint data processing module is configured to correlate the first and second candidate breakpoints by:
- identifying the first breakpoint from the DNA-SEQ breakpoint detection step and the second breakpoint from the RNA-SEQ breakpoint detection steps that share a common location on a chromosome; and
- combining the identified first breakpoint and second breakpoint to generate a combined breakpoint list.

14. The system of claim 9, wherein the gene fusion data annotation module is configured to annotate the combined breakpoint list with biologically relevant information comprises:
- determining a location of the combined breakpoint on a gene transcript to identify a gene fusion that is associated with each of the combined breakpoint;
- performing a transcript maturity analysis for the gene fusion to predict maturity of the gene fusion transcript; and
- annotating each of the combined breakpoint with information on the associated gene fusion and the predicted maturity of the gene fusion transcript.

15. The system of claim 14, wherein the gene fusion data annotation module is configured to annotate the combined breakpoint with clinically relevant information by:
- annotating the combined breakpoint list with information on whether the gene fusion is missing a conserved domain from a tumor suppressor gene or contains a conserved domain of an oncogene by comparing the gene fusion against a first database containing such information; and
- annotating the gene fusion data with information on a specific cancer therapy for a type of cancer that is associated with the gene fusion by comparing the gene fusion against second database containing such information.

16. The system of claim 9, wherein the RNA-SEQ breakpoint detection module is configured to perform step (b) before or concurrently with the DNA-SEQ breakpoint detection module performing step (a).

17. A non-transitory computer-readable medium comprising instructions which, when implemented by one or more computers, cause the one or more computers to perform steps including:
- (a) detecting a first candidate breakpoint based on a DNA-SEQ data set by comparing the DNA-SEQ data set to a DNA reference sequence data set;
- (b) detecting a second candidate breakpoint based on a RNA-SEQ data set by comparing the RNA-SEQ data set to both a DNA reference sequence data set and a RNA reference data set;
- (c) correlating the first and second candidate breakpoints to generate a combined breakpoint list, characterized by a higher threshold specificity;

(d) annotating the combined breakpoint list with biologically and clinically relevant information to generate an annotated gene fusion data set, wherein the combined breakpoint list of step (c) has a lower false-positive breakpoint detection rate compared to a false-positive breakpoint detection rate in the absence of the correlation in step (c), wherein the annotated gene fusion data set is suitable for being used for having a clinical decision made, and wherein the DNA-SEQ data set and the RNA-SEQ data set are each obtained from a different sequencing platform and standardized into a common read format before detecting the first or second candidate breakpoints.

18. The non-transitory computer-readable medium of claim 17, wherein the step of comparing the DNA-SEQ data set to DNA reference sequence data set in step (a) comprises:

optimizing structure of the DNA-SEQ data set by sorting, removing duplicates from, and indexing the DNA-SEQ data set;

aligning the DNA-SEQ data set with the DNA reference sequence data set;

determining a location of the candidate breakpoint relative to the DNA reference sequence data set; and collecting statistical evidence associated with the candidate breakpoint.

19. The non-transitory computer-readable medium of claim 17, wherein the step of comparing the RNA-SEQ data set to both DNA reference sequence data set and RNA reference sequence data set in step (b) comprises:

aligning the RNA-SEQ data set with the DNA reference sequence data set;

optimizing structure of the RNA-SEQ data set by sorting and removing duplicates from the RNA-SEQ data set;

aligning the RNA-SEQ data set with the RNA reference sequence data set;

optimizing structure of the RNA-SEQ data set by sorting and removing duplicates from the RNA-SEQ data set;

determining a location of the candidate breakpoint relative to the RNA reference sequence data set; and collecting statistical evidence associated with the candidate breakpoint.

20. The non-transitory computer-readable medium of claim 17, wherein the step of correlating the first and second candidate breakpoints in step (c) comprises performing a cascading filtering, the cascading filtering comprising:

removing the candidate breakpoint having low coverage and high breakpoints reported around the candidate breakpoint;

removing the candidate breakpoint having large portion of supporting reads with low mapping quality;

removing the candidate breakpoint having bias-distributed supporting read along two genomic strands;

removing the candidate breakpoint with both ends located on homologous genes; and removing the candidate breakpoint with both ends located on adjacent genes.

21. The non-transitory computer-readable medium of claim 17, wherein the step of correlating the first and second candidate breakpoints in step (c) comprise:

identifying the first breakpoint from the DNA-SEQ breakpoint detection step and the second breakpoint from the RNA-SEQ breakpoint detection steps that share a common location on a chromosome; and combining the identified first breakpoint and second breakpoint to generate a combined breakpoint list.

22. The non-transitory computer-readable medium of claim 17, wherein the step of annotating the combined breakpoint list with biologically relevant information in step (d) comprises:

determining a location of the combined breakpoint on a gene transcript to identify a gene fusion that is associated with each of the combined breakpoint;

performing a transcript maturity analysis for the gene fusion to predict maturity of the gene fusion; and annotating each of the combined breakpoint with information on the associated gene fusion and the predicted maturity of the gene fusion.

23. The non-transitory computer-readable medium of claim 22, wherein the step of annotating the combined breakpoint list with clinically relevant information in step (d) comprises:

annotating the combined breakpoint list with information on whether the gene fusion is missing a conserved domain from a tumor suppressor gene or contains a conserved domain of an oncogene by comparing the gene fusion against a first database containing such information; and annotating the gene fusion data with information on a specific cancer therapy for a type of cancer that is associated with the gene fusion by comparing the gene fusion against second database containing such information.

24. The non-transitory computer-readable medium of claim 17, wherein step (b) is performed before or concurrently with step (a).

* * * * *